(12) United States Patent
Sawada et al.

(10) Patent No.: US 11,765,313 B2
(45) Date of Patent: Sep. 19, 2023

(54) RADIATION IMAGE CAPTURING APPARATUS AND RADIATION IMAGE CAPTURING SYSTEM

(71) Applicant: CANON KABUSHIKI KAISHA, Tokyo (JP)

(72) Inventors: Satoru Sawada, Kanagawa (JP); Kentaro Fujiyoshi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/849,022

(22) Filed: Jun. 24, 2022

(65) Prior Publication Data

US 2022/0321805 A1 Oct. 6, 2022

Related U.S. Application Data

(63) Continuation of application No. 17/234,254, filed on Apr. 19, 2021, now Pat. No. 11,445,130, which is a continuation of application No. PCT/JP2019/039484, filed on Oct. 7, 2019.

(30) Foreign Application Priority Data

Oct. 25, 2018 (JP) ................................. 2018-200584

(51) Int. Cl.
*H04N 5/32* (2023.01)
*G01T 1/29* (2006.01)
*G01T 1/24* (2006.01)
*H04N 25/74* (2023.01)
*H04N 25/75* (2023.01)

(52) U.S. Cl.
CPC ............... *H04N 5/32* (2013.01); *G01T 1/247* (2013.01); *G01T 1/2921* (2013.01); *H04N 25/74* (2023.01); *H04N 25/75* (2023.01)

(58) Field of Classification Search
None
See application file for complete search history.

(56) References Cited

U.S. PATENT DOCUMENTS 11,445,130 B2 * 9/2022 Sawada ................ H04N 5/3696

* cited by examiner

*Primary Examiner* — Edwin C Gunberg
(74) *Attorney, Agent, or Firm* — Canon U.S.A., Inc., IP Division

(57) ABSTRACT

A radiation image capturing apparatus includes, as a plurality of pixels two-dimensionally arranged in an image capturing area, a plurality of image pixels configured to output electric signals for acquiring a radiation image and a plurality of detection pixels configured to output electric signals for detecting information about irradiation of the image capturing area with the irradiation. The plurality of detection pixels is arranged as a line-shaped detection pixel group in the image capturing area, and a plurality of detection driving lines is connected to the line-shaped detection pixel group. A readout circuit reads out, at different timings, the electric signals group by group to each of which a different one of the plurality of detection driving lines is connected in the line-shaped detection pixel group.

14 Claims, 8 Drawing Sheets

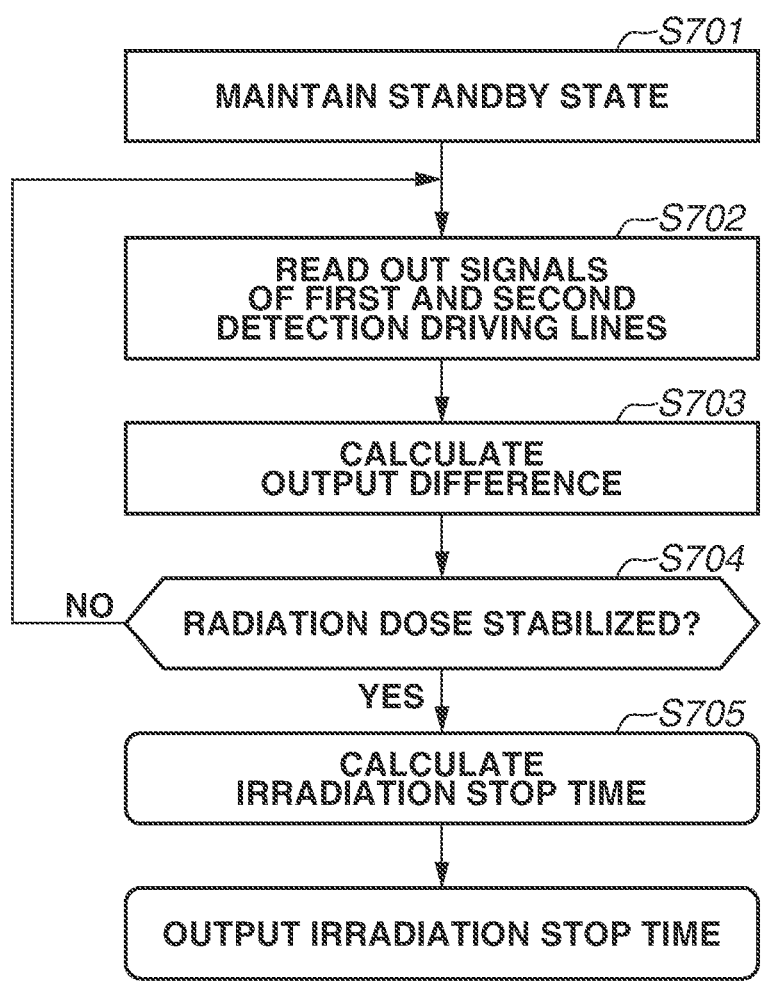

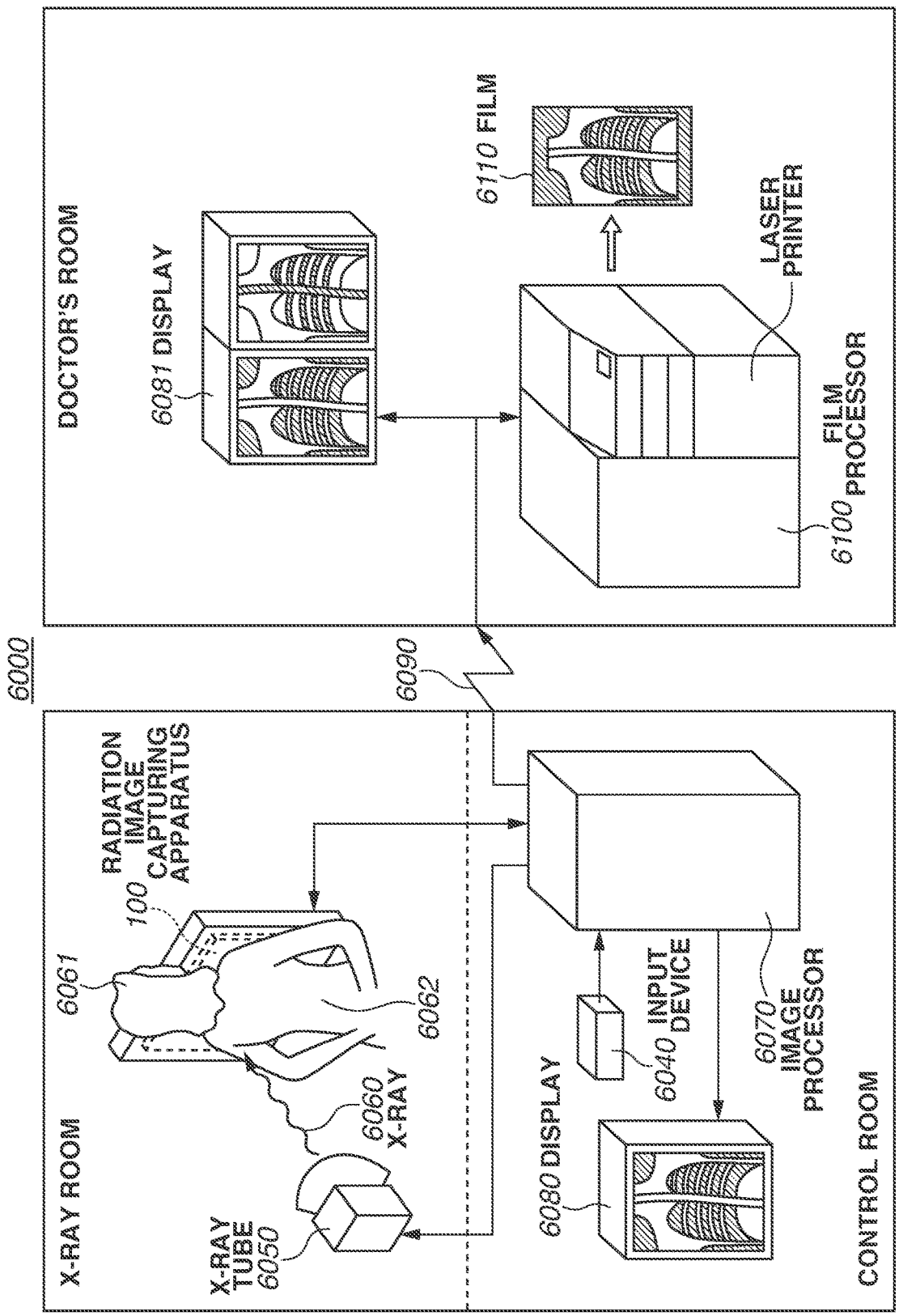

RADIATION IMAGE CAPTURING APPARATUS AND RADIATION IMAGE CAPTURING SYSTEM

CROSS-REFERENCE TO RELATED APPLICATIONS

This application is a Continuation of U.S. patent application Ser. No. 17/234,254, filed Apr. 19, 2021, which is a Continuation of International Patent Application No. PCT/JP2019/039484, filed Oct. 7, 2019, which claims the benefit of Japanese Patent Application No. 2018-200584, filed Oct. 25, 2018, both of which are hereby incorporated by reference herein in their entirety.

BACKGROUND OF THE INVENTION

Field of the Invention

The present invention relates to a radiation image capturing apparatus and a radiation image capturing system.

Background Art

A radiation image capturing apparatus that includes an image capturing area in which pixels each including a conversion element which converts radiation into charges and a switch element, such as a thin-film transistor, are two-dimensionally arranged has been widely used. Recently, making such a radiation image capturing apparatus multi-functional has been contemplated, and incorporation of an automatic exposure control (AEC) function has been contemplated as one of the functions. The AEC function can be used to detect information about irradiation of the image capturing area with radiation, for example, information about the starting of the image capturing area with radiation from a radiation source, the ending of the irradiation with the radiation (including determination of end timing), irradiation intensity of the radiation, and a dose (including cumulative dose) of the radiation.

Examples of the radiation image capturing apparatus for detecting such information about irradiation with radiation includes a radiation image capturing apparatus discussed in PTL 1. PTL 1 discusses a radiation image capturing apparatus that includes a plurality of pixels for acquiring a radiation image and a plurality of sensor units for detecting radiation. Each of the sensor units includes a sensor that converts the radiation into electric signals and accumulates the electric signals during a signal accumulation period. More specifically, the radiation image capturing apparatus discussed in PTL 1 includes a control unit and a signal processing unit. The control unit controls the plurality of sensor units such that the signal accumulation periods of the respective sensors of the plurality of sensor units each have a first time and are shifted from one another by a second time shorter than the first time. The signal processing unit outputs information about incident radiation, based on the signals from the plurality of sensor units controlled by the control unit in a cycle of the second time.

To enable the radiation image capturing apparatus to accurately detect the information about irradiation with radiation, such as the irradiation intensity of the radiation, which is changing every instant, it is necessary to increase a readout frequency of the signals from the sensors for detection of the information, namely, a detection frequency (time resolution).

When the above-described detection frequency is increased, however, the signal accumulation period of each of the sensors becomes short. As a result, a signal-to-noise ratio (SNR) in readout of the signals from the sensors is lowered, and detection accuracy of the information about irradiation with radiation decreases. In other words, the detection frequency and the detection accuracy of the information about irradiation with radiation have trade-off relationship.

In this regard, the above-described radiation image capturing apparatus discussed in PTL 1 is insufficient as the technique for improving the detection accuracy of the information about irradiation with radiation while increasing the detection frequency of the information.

The present invention is made in consideration of such issues, and is directed to a mechanism that can improve detection accuracy of information about irradiation with radiation while increasing detection frequency of the information.

CITATION LIST

Patent Literature

PTL 1: Japanese Patent Laid-Open No. 2016-10066

SUMMARY OF THE INVENTION

A radiation image capturing apparatus includes a plurality of pixels two-dimensionally arranged in an image capturing area and configured to convert incident radiation into electric signals; a plurality of driving lines for driving the plurality of pixels, and a readout circuit configured to read out the electric signals of the plurality of pixels. The plurality of pixels includes a plurality of first pixels configured to output the electric signals for acquiring a radiation image and a plurality of second pixels configured to output the electric signals for detecting information about irradiation of the image capturing area with the irradiation. The plurality of second pixels is arranged as a line-shaped second pixel group in the image capturing area, and the plurality of driving lines is connected to the line-shaped second pixel group. The readout circuit reads out, at different timings, the electric signals group by group to each of which a different one of the plurality of driving lines is connected in the line-shaped second pixel group.

The present invention includes a radiation image capturing system that includes the above-described radiation image capturing apparatus and a processing apparatus processing signals from the radiation image capturing apparatus.

Further features of the present invention will become apparent from the following description of exemplary embodiments with reference to the attached drawings.

BRIEF DESCRIPTION OF THE DRAWINGS

FIG. 7 is a flowchart illustrating an example of a processing procedure in which irradiation of radiation is detected, irradiation intensity is determined, and an irradiation stop time is output, in the radiation image capturing apparatus according to the exemplary embodiment of the present invention.

FIG. 8 is a diagram illustrating an example of a schematic configuration of a radiation image capturing system (X-ray image capturing system) including the radiation image capturing apparatus according to the exemplary embodiment of the present invention.

DESCRIPTION OF THE EMBODIMENTS

An exemplary embodiment of the present invention will be described below with reference to the drawings. In the present specification, radiation includes, in addition to α-rays, β-rays, and γ-rays that are beams formed by particles (including photons) emitted by radioactive decay, beams having equivalent or more energy, such as X-rays, particle rays, and cosmic rays.

In the exemplary embodiment of the present invention described below, a description on the assumption of automatic exposure control (AEC) is mainly given; however, the technique of the present exemplary embodiment may be used for radiation irradiation measurement (monitor) used in AEC, and the radiation image capturing apparatus itself may not perform the AEC. In the exemplary embodiment of the present invention described below, "information about irradiation of radiation to image capturing area" includes information about at least one of irradiation start of radiation to the image capturing area, irradiation end of the radiation to the image capturing area (including determination of end timing), irradiation intensity of the radiation to the image capturing area, and a dose (including cumulative dose) of the radiation to the image capturing area.

Figure 1:
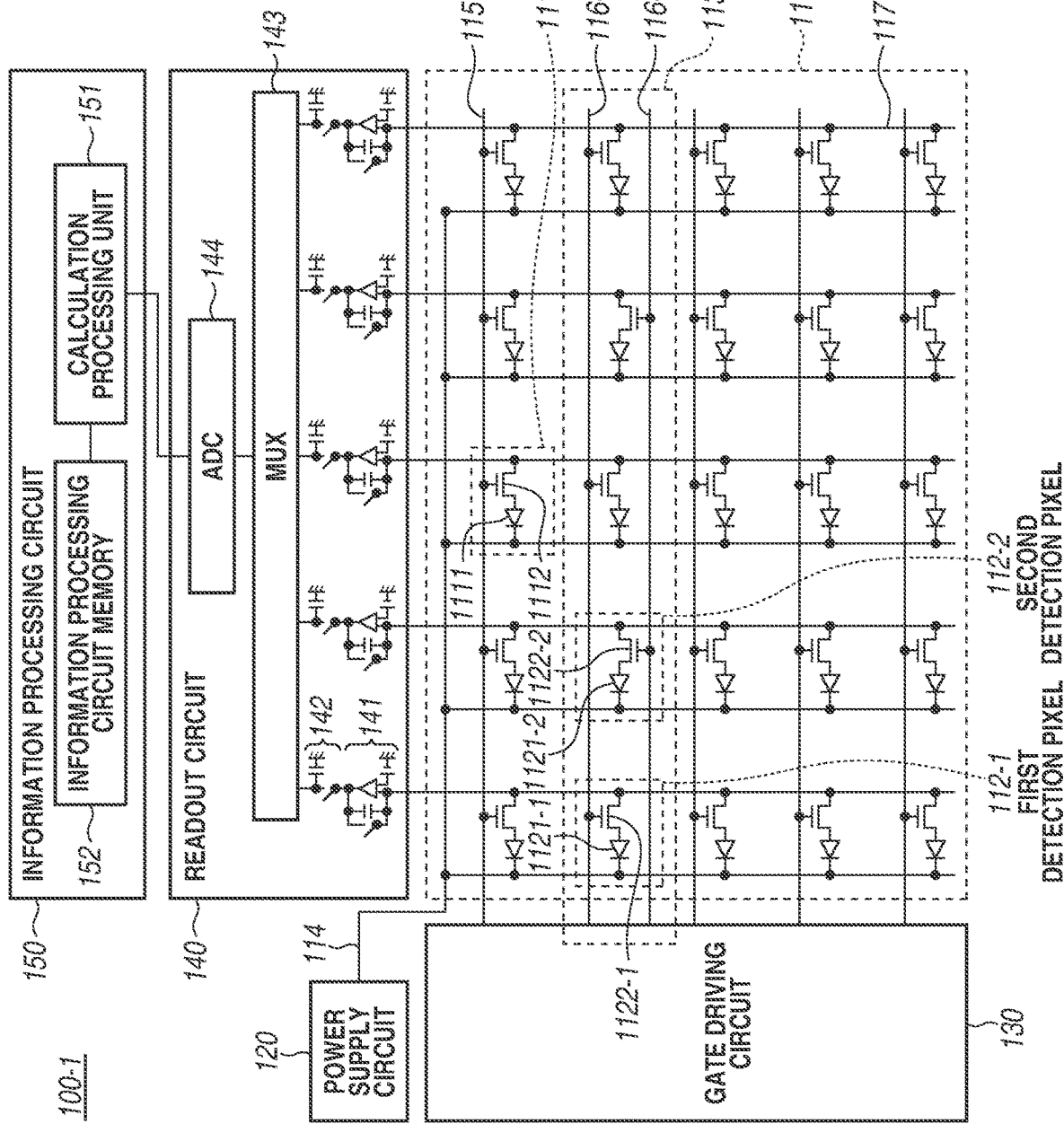
FIG. 1 is an equivalent circuit diagram illustrating a first configuration example of a radiation image capturing apparatus according to an exemplary embodiment of the present invention.

FIG. 1 is an equivalent circuit diagram illustrating a first configuration example of a radiation image capturing apparatus 100 according to the exemplary embodiment of the present invention. In the following, the radiation image capturing apparatus 100 of the first configuration example illustrated in FIG. 1 is referred to as a "radiation image capturing apparatus 100-1".

As illustrated in FIG. 1, the radiation image capturing apparatus 100-1 includes an image capturing area 110, a power supply circuit 120, a gate driving circuit 130, a readout circuit 140, and an information processing circuit 150.

In the image capturing area 110, a plurality of image pixels 111 and a plurality of detection pixels 112 are provided as a plurality of pixels that is two-dimensionally arranged (more specifically, in matrix shape) on a substrate and converts incident radiation into electric signals. The plurality of detection pixels 112 are arranged as a line-shaped detection pixel group 113 in the image capturing area 110.

The image pixels 111 are first pixels which output electric signals to acquire a radiation image. In this example, among the plurality of pixels two-dimensionally arranged in the image capturing area 110, the pixels other than the line-shaped detection pixel group 113 are image pixels 111; however, the pixels are not limited thereto in the present exemplary embodiment. The image pixels 111 are supplied with power from the power supply circuit 120 through power supply lines 114, and are supplied with driving signals from the gate driving circuit 130 through image driving lines 115, thereby being driven and controlled. Each of the image pixels 111 includes an equivalent circuit of a conversion element 1111 which converts the incident radiation into an electric signal (charge) and a switch element 1112 which outputs the resultant electric signal to outside. The electric signals output from the image pixels 111 are read out to the readout circuit 140 through signal lines 117, and the radiation image is acquired by subsequent processing.

The detection pixels 112 are second pixels which output electric signals for detecting information about irradiation of the image capturing area 110 with radiation. In this case, the line-shaped detection pixel group 113 is a line-shaped second pixel group. The detection pixels 112 are supplied with power from the power supply circuit 120 through the power supply lines 114, and are supplied with driving signals from the gate driving circuit 130 through detection driving lines 116, thereby being driven and controlled. In the present exemplary embodiment, the line-shaped detection pixel group 113 is connected to the plurality of detection driving lines 116 for driving the plurality of detection pixels 112. More specifically, FIG. 1 illustrates an example in which the line-shaped detection pixel group 113 is connected to two detection driving lines 116 that are a first detection driving line 116-1 connected to detection pixels 112-1 of a first group, and a second detection driving line 116-2 connected to detection pixels 112-2 of a second group. In the example illustrated in FIG. 1, the first detection driving line 116-1 is connected to the detection pixels 112-1 in each of the first column, the third column, and the fifth column from the left, and the second detection driving line 116-2 is connected to the detection pixels 112-2 in each of the second column and the fourth column from the left. In other words, in the line-shaped detection pixel group 113, the two detection pixels 112-1 and 112-2 adjacent in a direction of the line defined by the line-shaped detection pixel group 113 (lateral direction (row direction) of image capturing area 110) are respectively connected to the different detection driving lines 116-1 and 116-2. In the present exemplary embodiment, such a configuration enables the electric signals of the line-shaped detection pixel group 113 to be separately read out with the two detection driving lines 116. Although FIG. 1 illustrates the example in which the two detection driving lines are provided as the plurality of detection driving lines 116 connected to the line-shaped detection pixel group 113, the detection driving lines are not limited thereto in the present exemplary embodiment, and for example, three or more detection driving lines may be provided. Each of the detection pixels 112-1 includes an equivalent circuit of a conversion element 1121-1 which converts the incident radiation into an electric signal (charge) and a switch element 1122-1 which outputs the electric signal to outside. Similarly, each of the detection pixels 112-2 includes an equivalent circuit of a conversion element 1121-2 which converts the incident radiation into an electric signal (charge) and a switch element 1122-2 outputting the electric signal to outside. The electric signals output from the detection pixels 112-1 of the first group and the electric signals output from the detection pixels 112-2 of the second group are read out to the readout circuit 140 through the signal lines 117 at different timings, and the information about irradiation of the image capturing area 110 with the radiation is acquired through subsequent processing. Arranging such detection pixels 112 makes it possible to incorporate an automatic exposure control (AEC) function in the radiation image capturing apparatus 100. The signals of the detection pixels 112 may be used to acquire the radiation image. In other words, a part of the image pixels 111 may be used as the detection pixels 112.

Although, in FIG. 1, the pixels of 5 rows×5 columns are illustrated in the image capturing area 110, these pixels illustratively represent a part of the pixels actually arranged in the image capturing area of the radiation image capturing apparatus 100. Further, only a single line-shaped detection pixel group 113 may be disposed in the image capturing area 110 as illustrated in FIG. 1, or a plurality of line-shaped detection pixel groups 113 may be disposed in the image capturing area 110.

The power supply circuit 120 is disposed in a peripheral area of the image capturing area 110, and supplies power to each of the image pixels 111 and each of the detection pixels 112 provided in the image capturing area 110 through the power supply lines 114.

The gate driving circuit 130 is disposed in a peripheral area of the image capturing area 110, and supplies driving signals to the image pixels 111 through the connected image driving lines 115 that are connected thereto, among the plurality of image driving lines 115. At this time, the gate driving circuit 130 can sequentially (e.g., in order from above in FIG. 1) supply the driving signals to the plurality of image driving lines 115. The gate driving circuit 130 supplies the driving signals to the detection pixels 112 through the detection driving line 116 that is connected thereto among the plurality of detection driving lines 116 (first detection driving line 116-1 and second detection driving line 116-2). At this time, the gate driving circuit 130 supplies the driving signals to the plurality of detection driving lines 116 connected to the line-shaped detection pixel group 113 at different timings. In the example illustrated in FIG. 1, the gate driving circuit 130 is equivalent to a driving signal supply circuit that supplies the driving signals to the detection driving lines 116 (first detection driving line 116-1 and second detection driving line 116-2).

The readout circuit 140 is disposed in a peripheral area of the image capturing area 110, and reads out the electric signals from the image pixels 111 and the detection pixels 112 provided in the image capturing area 110 through the plurality of signal lines 117. At this time, as illustrated in FIG. 1, the plurality of signal lines 117 is disposed to intersect with (preferably, orthogonal to) the plurality of image driving lines 115 and the plurality of detection driving lines 116. In the present exemplary embodiment, the readout circuit 140 reads out, at different timings, the electric signals from each of the groups connected to the respective detection driving lines 116 in the line-shaped detection pixel group 113 (i.e., first group of detection pixels 112-1 connected to first detection driving line 116-1 and second group of detection pixels 112-2 connected to detection driving line 116-2). As illustrated in FIG. 1, the readout circuit 140 includes amplification circuits 141, sample-and-hold circuits 142, a multiplexer (MUX) 143, and an analog-to-digital converter (ADC) 144. The plurality of amplification circuits 141 and the plurality of sample-and-hold circuits 142 are provided in correspondence with the signal lines 117. The amplification circuits 141 amplify the electric signals output through the signal lines 117, and the sample-and-hold circuits 142 sample and hold the electric signals amplified by the amplification circuits 141. The MUX 143 sequentially selects the electric signals output in parallel from the sample-and-hold circuits 142, and outputs the electric signals to the ADC 144. The ADC 144 converts the analog electric signals output from the MUX 143 into digital electric signals.

As illustrated in FIG. 1, the information processing circuit 150 includes a calculation processing unit 151 and an information processing circuit memory 152. The calculation processing unit 151 performs various types of calculation processing on the electric signals output from the ADC 144. For example, the calculation processing unit 151 performs predetermined calculation processing on the electric signals output from the ADC 144 to generate the information about irradiation of the image capturing area 110 with radiation. The information processing circuit memory 152 stores the information acquired as a result of the various types of calculation processing by the calculation processing unit 151.

While FIG. 1 illustrates the example including the readout circuit 140 and the information processing circuit 150 as the signal processing circuits, the signal processing circuit is not limited thereto in the present exemplary embodiment. For example, the readout circuit 140 and the information processing circuit 150 may be integrally configured as one signal processing circuit.

Figure 2:
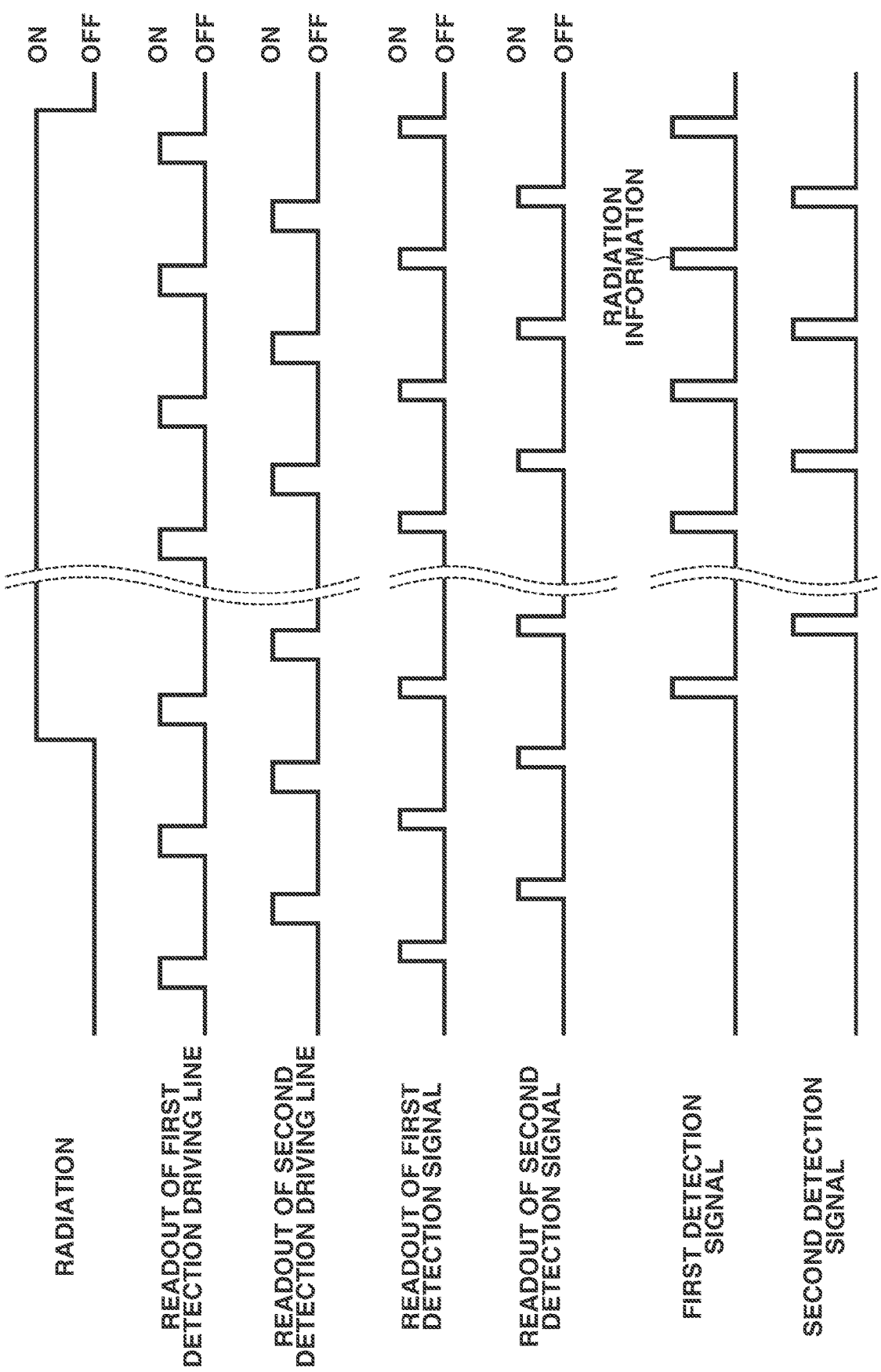
FIG. 2 is a timing chart illustrating an example of a driving method during radiation irradiation in the radiation image capturing apparatus according to the exemplary embodiment of the present invention.

FIG. 2 is a timing chart illustrating an example of a driving method during radiation irradiation in the radiation image capturing apparatus 100 according to the exemplary embodiment of the present invention. FIG. 2 illustrates, from above, a timing when the radiation image capturing apparatus 100 (more specifically, image capturing area 110) is irradiated with the radiation from a radiation source, a timing when the switch elements 1122-1 of the detection pixels 112-1 of the first group are turned on, a timing when the switch elements 1122-2 of the detection pixels 112-2 of the second group are turned on, a timing when first detection signals as the electric signals of the detection pixels 112-1 of the first group are read out through the signal lines 117, and a timing when second detection signals as the electric signals of the detection pixels 112-2 of the second group are read out through the signal lines 117. Further, FIG. 2 illustrates signal output for the information (radiation information) about irradiation with the radiation based on the first detection signals and signal output for the information (radiation information) about irradiation with the radiation based on the second detection signals.

More specifically, in FIG. 2, after the gate driving circuit 130 turns on the switch elements 1122-1 of the detection pixels 112-1 connected to the first detection driving line 116-1, the readout circuit 140 reads out the electric signals of the detection pixels 112-1 through the signal lines 117. Next, after the gate driving circuit 130 turns on the switch elements 1122-2 of the detection pixels 112-2 connected to the second detection driving line 116-2, the readout circuit 140 reads out the electric signals of the detection pixels 112-2 through the signal lines 117. Thereafter, the first detection driving line 116-1 operates in a similar manner, and the second detection driving line 116-2 also operates in a similar manner. In such a manner, in the line-shaped detection pixel group 113 illustrated in FIG. 1, the first detection driving line 116-1 and the second detection line 116-2 are controlled, and the information (radiation information) about irradiation with the radiation based on the electric signals of the detection pixels 112-1 of the first group and the information (radiation information) about irradiation with the radiation based on the electric signals of the detection pixels 112-2 of the second group are alternately read out at different timings. This makes it possible to elongate the accumulation time of the electric signals (charges) of the detection pixels 112-1 of the first group and the accumulation time of the electric signals (charges) of the detection pixels 112-2 of the second group. Since the plurality of detection driving lines 116-1 and 116-2 is connected to the line-shaped detection pixel group 113, even in a case where the electric signals of each of the detection pixels 112-1 and the detection pixels 112-2 are read out at the same intervals as in a case where one driving line is used, about twice the number of signals are obtainable as the detection signals. Accordingly, the configuration of the present exemplary embodiment makes it possible to improve the detection accuracy of the information about irradiation with the radiation (radiation information) while increasing the detection frequency of the information. For example, in a case where, as a comparative example, the line-shaped detection pixel group 113 is controlled by using a single detection driving line and the driving timings are set to be the same as those in the present exemplary embodiment, an amount of obtainable information about irradiation with the radiation (radiation information) is about half that in the present exemplary embodiment. In this comparative example, to obtain an amount of information about irradiation with the radiation (radiation information) equivalent to that in the present exemplary embodiment, it is necessary to substantially double the driving timings, and thus, it is difficult to improve the detection accuracy of the radiation information while increasing the detection frequency of the radiation information.

Figure 3:
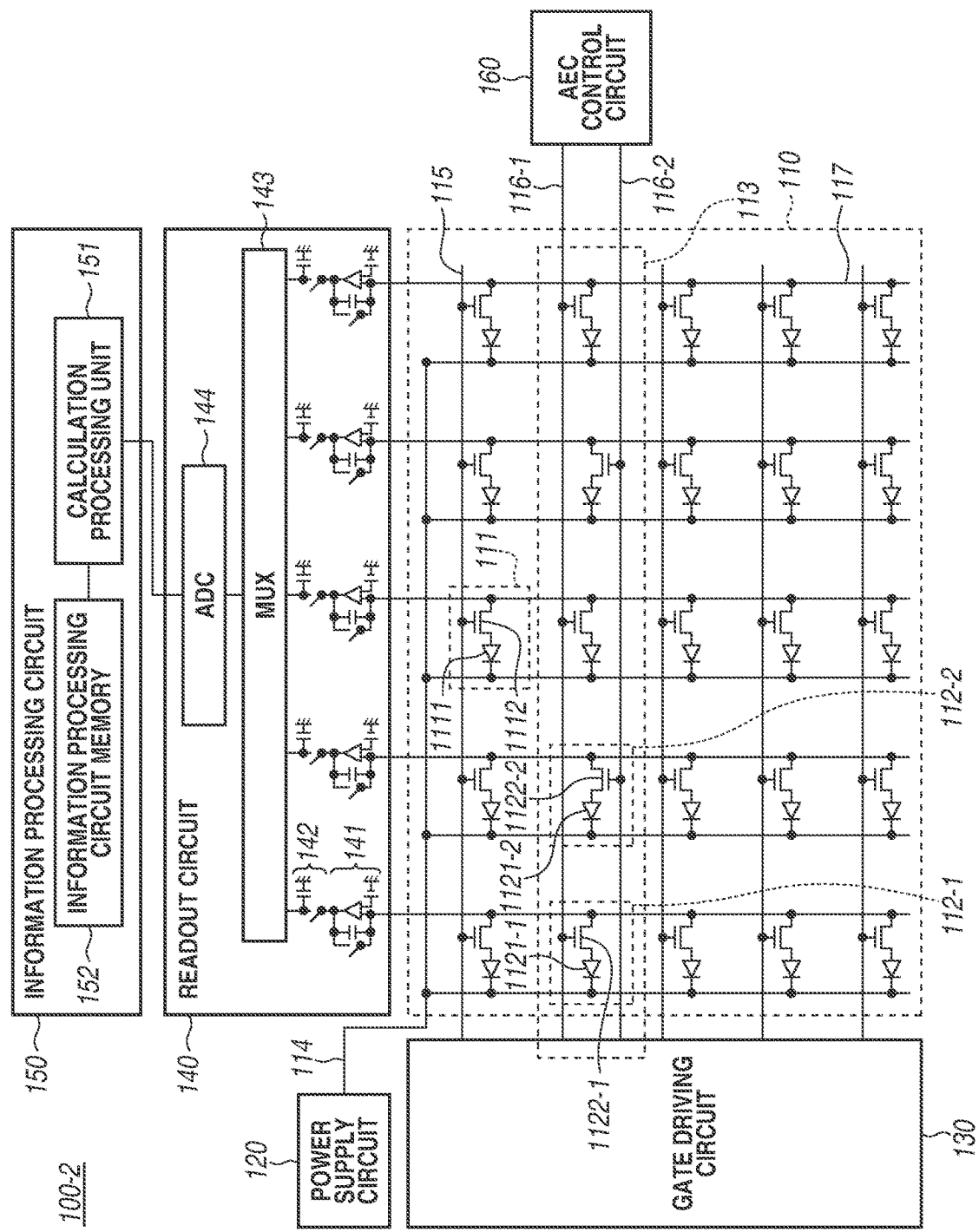
FIG. 3 is an equivalent circuit diagram illustrating a second configuration example of the radiation image capturing apparatus according to the exemplary embodiment of the present invention.

FIG. 3 is an equivalent circuit diagram illustrating a second configuration example of the radiation image capturing apparatus 100 according to the exemplary embodiment of the present invention. In the following, the radiation image capturing apparatus 100 in the second configuration example illustrated in FIG. 3 is referred to as a "radiation image capturing apparatus 100-2". In FIG. 3, components similar to the components illustrated in FIG. 1 are denoted by the same reference numerals, and detailed descriptions of the components are omitted.

The radiation image capturing apparatus 100-2 illustrated in FIG. 3 has a configuration in which an AEC control circuit 160 is added to the configuration of the radiation image capturing apparatus 100-1 illustrated in FIG. 1. More specifically, in the radiation image capturing apparatus 100-1 illustrated in FIG. 1, the gate driving circuit 130 drives both of the image pixels 111 and the detection pixels 112. In contrast, in the radiation image capturing apparatus 100-2 illustrated in FIG. 3, the gate driving circuit 130 drives the image pixels 111, and the AEC control circuit 160, which is different from this gate driving circuit 130, drives the detection pixels 112. The radiation image capturing apparatus 100-2 illustrated in FIG. 3 may have the configuration same as the configuration of the radiation image capturing apparatus 100-1 illustrated in FIG. 1 except that the AEC control circuit 160 is added. In the example illustrated in FIG. 3, the AEC control circuit 160 corresponds to a driving signal supply circuit which supplies driving signals to the detection driving lines 116 (first detection driving line 116-1 and second detection driving line 116-2).

The radiation image capturing apparatus 100-2 illustrated in FIG. 3 excludes the need for complicated operation of the gate driving circuit 130, unlike the radiation image capturing apparatus 100-1 illustrated in FIG. 1, and thus, design of the gate driving circuit 130 is facilitated. For example, in the radiation image capturing apparatus 100-2 illustrated in FIG. 3, the AEC control circuit 160 is driven during a period from when radiation is emitted to when readout of the electric signals relating to the information about irradiation with the radiation (radiation information) in the detection pixels 112. Next, when the electric signals relating to the radiation image are read out from the image pixels 111, the AEC control circuit 160 may be stopped, and the gate driving circuit 130 may be driven to sequentially read out the electric signals from each row. The configuration of causing a circuit in the peripheral areas to operate separately for the detection pixels 112 and the image pixels 111 is not limited to the control circuit. For example, a readout circuit which reads the electric signals of the detection pixels 112 may be provided separately from the readout circuit which reads the electric signals of the image pixels 111, and processing may be performed.

Figure 4A:
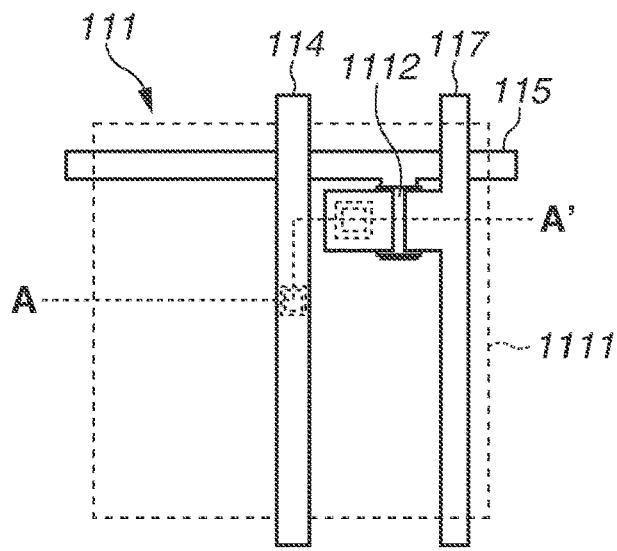
FIG. 4A is a schematic plan view of an image pixel, a detection pixel of a first group, and a detection pixel of a second group of the radiation image capturing apparatus according to the exemplary embodiment of the present invention.
Figure 4B:
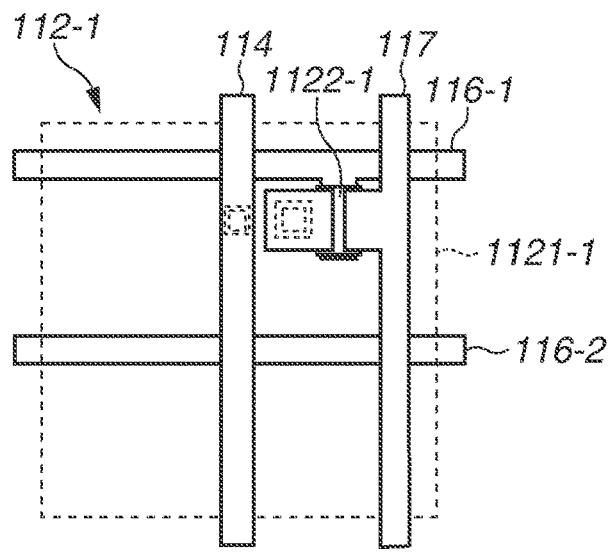
FIG. 4B is a schematic plan view of an image pixel, a detection pixel of a first group, and a detection pixel of a second group of the radiation image capturing apparatus according to the exemplary embodiment of the present invention.
Figure 4C:
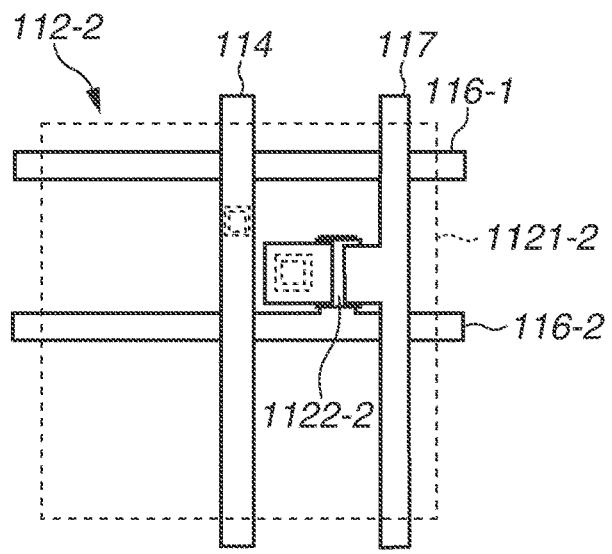
FIG. 4C is a schematic plan view of an image pixel, a detection pixel of a first group, and a detection pixel of a second group of the radiation image capturing apparatus according to the exemplary embodiment of the present invention.

FIGS. 4A to 4C are schematic plan views respectively illustrating an image pixel 111, a detection pixel 112-1 of the first group, and a detection pixel 112-2 of the second group of the radiation image capturing apparatus 100 according to the exemplary embodiment of the present invention. More specifically, FIG. 4A is a schematic plan view of an image pixel 111, FIG. 4B is a schematic plan view of a detection pixel 112-1 of the first group, and FIG. 4C is a schematic plan view of a detection pixel 112-2 of the second group. In FIGS. 4A to 4C, components similar to the components illustrated in FIG. 1 and FIG. 3 are denoted by the same reference numerals, and detailed descriptions of the components are omitted.

Here, a case where the radiation image capturing apparatus 100 is an indirect radiation image capturing apparatus will be described. In this case, a scintillator (not illustrated) is disposed on an upper part of the image pixels 111 and the detection pixels 112 (on radiation incident side) of the image capturing area 110 including the image pixels 111 and the detection pixels 112.

As illustrated in FIG. 4A, each of the image pixels 111 includes, as the conversion element 1111, an image photoelectric conversion element that converts light converted from the radiation by the scintillator, into the electric signal. Below the image photoelectric conversion element provided as the conversion element 1111, an image thin-film transistor (TFT) as the switch element 1112 and various lines are provided. The electric signal generated by the image photoelectric conversion element is output to the corresponding signal line 117 via the switch element 1112 when the switch element 1112 is turned on by the driving signal of the corresponding image driving line 115. An upper electrode of the image photoelectric conversion element is connected to the corresponding power supply line 114 for applying a predetermined voltage. The detection driving lines 116 may pass below the image photoelectric conversion element.

As illustrated in FIG. 4B, in each of the detection pixels 112-1 of the first group, while the first detection driving line 116-1 and the second detection driving line 116-2 are disposed, each of the detection pixels 112-1 of the first group is connected only to the first detection driving line 116-1 and the second detection driving line 116-2 is just laid. In the configuration of FIG. 4B, the configuration other than the detection driving lines 116 is basically the same as the configuration of each of the image pixels 111 as illustrated in FIG. 4A.

As illustrated in FIG. 4C, in each of the detection pixels 112-2, while the first detection driving line 116-1 and the second detection driving line 116-2 are disposed, each of the detection pixels 112-2 of the second group is connected only to the second detection driving line 116-2, and the first detection driving line 116-1 is just laid. In the configuration of FIG. 4C, the configuration other than the detection driving lines 116 is basically the same as the configuration of each of the image pixels 111 as illustrated in FIG. 4A.

Figure 5:
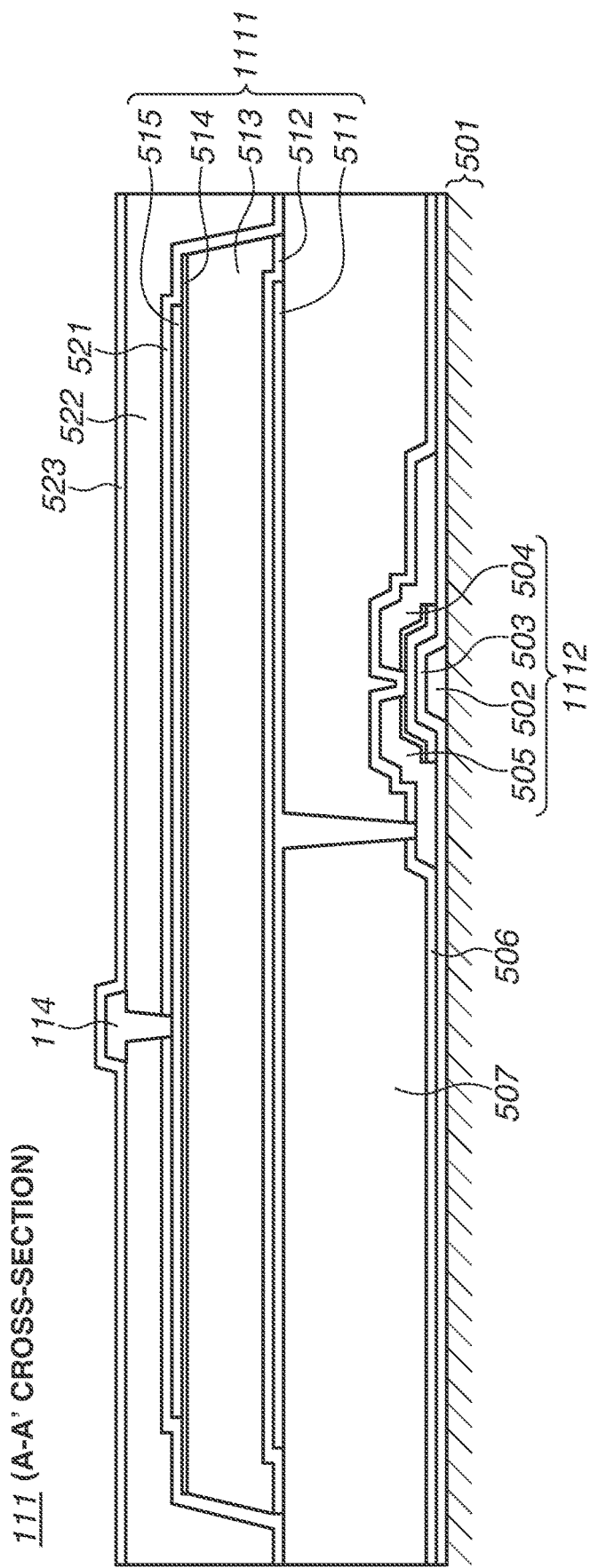
FIG. 5 is a cross-sectional view taken along line A-A' of the image pixel illustrated in FIG. 4A.

FIG. 5 is a cross-sectional view taken along line A-A' of an image pixel 111 illustrated in FIG. 4A. In FIG. 5, components similar to those illustrated in FIG. 4A are denoted by the same reference numerals, and detailed descriptions of the components are omitted. The pixels and the elements are provided on a substrate 501 of the image capturing area 110. In the present exemplary embodiment, an insulation substrate is used as the substrate 501. For example, a glass substrate or a plastic substrate may be used as the substrate 501. The image TFT as the switch element 1112 is provided on the substrate 501. In the present exemplary embodiment, an inverted staggered TFT is used. Alternatively, for example, a top gate TFT may be used. The switch element 1112 includes a gate electrode 502, an insulation film 503, a source electrode 504, and a drain electrode 505. The insulation film 503 may function as a gate insulation film in the image TFT. On the switch element 1112, the image photoelectric conversion element serving as the conversion element 1111 is disposed with a protection film 506 and an interlayer insulation film 507 in between. The image photoelectric conversion element serving as the conversion element 1111 has a structure in which a first impurity semiconductor layer 512, an intrinsic semiconductor layer 513, and a second impurity semiconductor layer 514 of a conductive type opposite to a conductive type of the first impurity semiconductor layer 512 are stacked in this order between a lower electrode 511 and an upper electrode 515. The first impurity semiconductor layer 512, the intrinsic semiconductor layer 513, and the impurity semiconductor layer 514 form a PIN photodiode, thus performing photoelectric conversion. While, in the present exemplary embodiment, the PIN photodiode is used for the photoelectric conversion elements, a metal-insulator-semiconductor (MIS) element may be used, for example. The power supply line 114 is arranged on the image photoelectric conversion element serving as the conversion element 1111 with a protection film 521 and an interlayer insulation film 522 in between. The image pixel 111 is covered with a protection film 523. The corresponding power supply line 114 is connected to the upper electrode 515 of the image photoelectric conversion element via a contact plug. The lower electrode 511 of the image photoelectric conversion element is connected to the drain electrode 505 of the image TFT. The electric signal (charge) generated by photoelectric conversion of the image photoelectric conversion element is output from the source electrode 504 to the corresponding signal line 117 when the image TFT is turned on by the gate electrode 502 connected to the image driving line 115.

Figure 6:
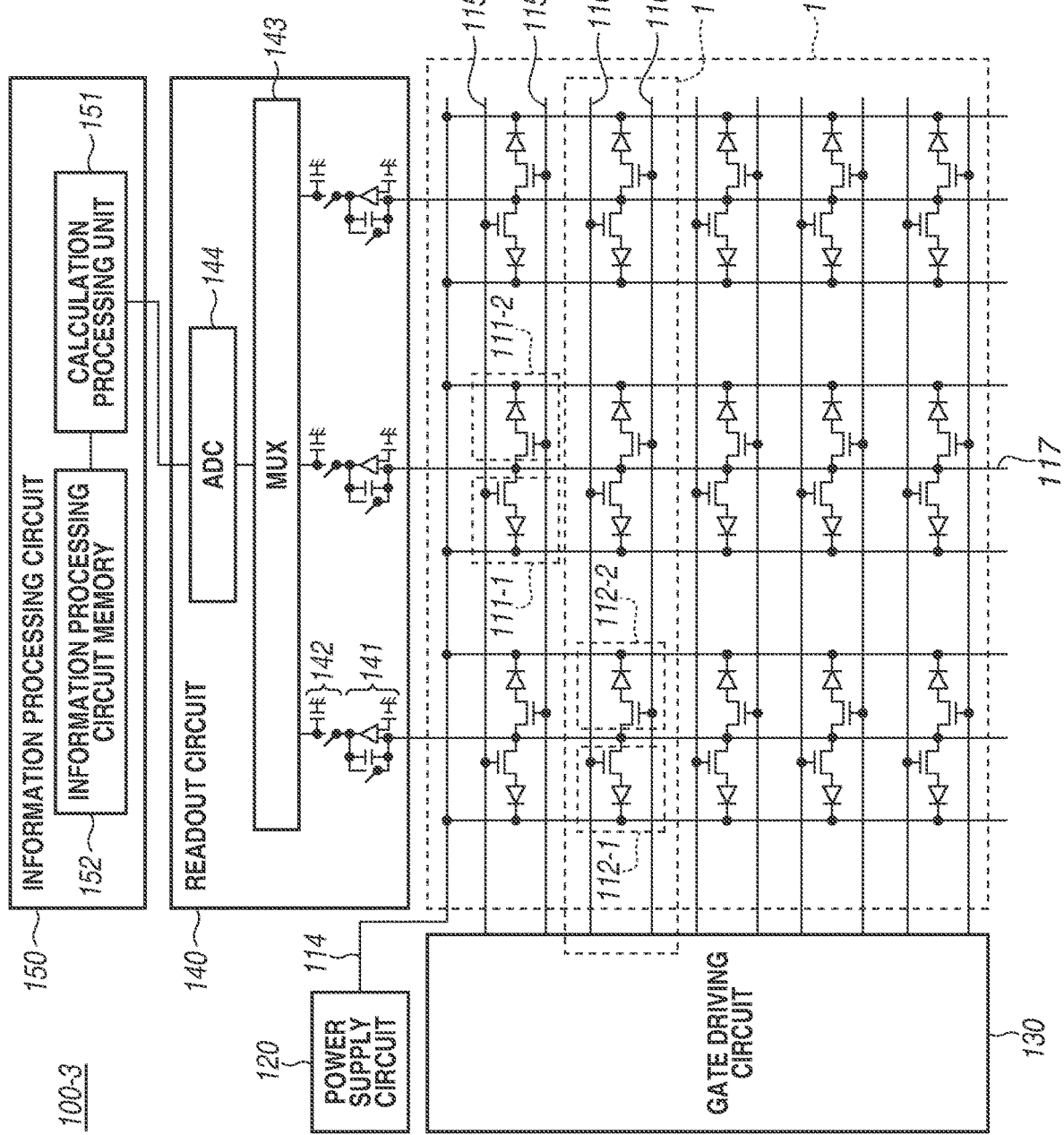
FIG. 6 is an equivalent circuit diagram illustrating a third configuration example of the radiation image capturing apparatus according to the exemplary embodiment of the present invention.

FIG. 6 is an equivalent circuit diagram illustrating a third configuration example of the radiation image capturing apparatus 100 according to the exemplary embodiment of the present invention. In the following, the radiation image capturing apparatus 100 in the third configuration example illustrated in FIG. 6 is referred to as a "radiation image capturing apparatus 100-3". In FIG. 6, components similar to the components illustrated in FIG. 1 are denoted by the same reference numerals, and detailed descriptions of the components are omitted.

The radiation image capturing apparatus 100-3 illustrated in FIG. 6 is different from the radiation image capturing apparatus 100-1 illustrated in FIG. 1 in that pixels of 5 rows×6 columns are provided in the image capturing area 110, and a single signal line 117 is shared by two adjacent pixels. More specifically, in the example illustrated in FIG. 6, the two detection pixels 112-1 and 112-2 adjacent in a direction of the line defined by the line-shaped detection pixel group 113 (in lateral direction (row direction) of image capturing area 110) are connected to a single signal line 117, and the two image pixels 111-1 and 111-2 adjacent in the direction of the line defined by the line-shaped detection pixel group 113 are connected to the single signal line 117. In FIG. 6, since the two image pixels 111-1 and 111-2 are connected to the single signal line 117, different image driving lines 115-1 and 115-2 are respectively connected to the image pixels 111-1 and 111-2. The configuration as illustrated in FIG. 6 makes it possible to simplify the circuit (e.g., readout circuit 140) relating to the signal lines 117, and to reduce the number of terminals connected to the circuit relating to the signal lines 117.

FIG. 7 is a flowchart illustrating an example of a processing procedure in which irradiation with radiation is detected, irradiation intensity is determined, and an irradiation stop time is output, in the radiation image capturing apparatus 100 according to the exemplary embodiment of the present invention. Initially, in step S701, the radiation image capturing apparatus 100 maintains a standby state. Thereafter, when irradiation with radiation is started, the processing proceeds to step S702. In step S702, the gate driving circuit 130 supplies driving signals to the first detection driving line 116-1 and the second detection driving line 116-2 at different timings, and the readout circuit 140 reads out the electric signals from the detection pixels 112-1 of the first group and the detection pixels 112-2 of the second group through the signal lines 117 at different timings. Subsequently, in step S703, the information processing circuit 150 (calculation processing unit 151) calculates a difference between the electric signals read out in step S702 (e.g., a difference between the electric signal read out from detection pixels 112-1 of first group and the electric signal read out from detection pixels 112-2 of second group). Subsequently, in step S704, the information processing circuit 150 (calculation processing unit 151) determines whether a dose of the radiation has been stabilized, based on the difference calculated in step S703. In a case where it is determined that the dose of the radiation has not been stabilized, in the determination in step S704 (NO in step S704), the processing returns to step S702. In a case where it is determined that the dose of the radiation has been stabilized (YES in step S704), the processing proceeds to step S705. In step S705, the information processing circuit 150 (calculation processing unit 151) calculates a time when the irradiation with radiation is to be stopped (irradiation stop time), based on the difference calculated in step S703. Subsequently, in step S706, the information processing circuit 150 (calculation processing unit 151) outputs information about the irradiation stop time calculated in step S705, to a controller (e.g., image processor 6070 in FIG. 8 described below) which controls a radiation source (e.g., X-ray tube 6050 in FIG. 8 described below). The controller stops the irradiation with radiation from the radiation source based on the irradiation stop time. The flowchart illustrated in FIG. 7 illustrates merely an example. Alternatively, the radiation image capturing apparatus 100 may output the information (radiation information) about monitored irradiation with radiation without performing calculation and output of the irradiation stop time, and the determination as to whether to stop the irradiation may be made by the radiation source emitting radiation and the controller which controls the radiation source, for example.

FIG. 8 is a diagram illustrating an example of a schematic configuration of a radiation image capturing system (X-ray image capturing system) 6000 including the radiation image capturing apparatus 100 according to the exemplary embodiment of the present invention. In the radiation image capturing system 6000 illustrated in FIG. 8, an X-ray 6060 that is radiation generated from the X-ray tube 6050 serving as the radiation source passes through a breast 6062 of a patient or subject 6061, and is incident on the radiation image capturing apparatus 100 according to the present exemplary embodiment. The incident X-ray 6060 includes information about the inside of the body of the patient or subject 6061. In the radiation image capturing apparatus 100, the conversion elements convert the X-ray 6060 into the electric signals (charges) based on incidence of the X-ray 6060, to obtain electric information. The obtained information is converted into a digital signal by the ADC 144, and the digital signal is output to the image processor 6070 that is a type of signal processing apparatus. The image processor 6070 performs various controls and various types of processing based on, for example, the information provided from an input device 6040. For example, the image processor 6070 controls the irradiation with the X-ray 6060 from the X-ray tube 6050 serving as the radiation source based on the information about the above-described irradiation stop time output from the radiation image capturing apparatus 100. In addition, the image processor 6070 generates an X-ray image by performing image processing on image signals based on the electric signals of the image pixels 111 output from the radiation image capturing apparatus 100, and displays the X-ray image on a display 6080 or transfers the X-ray image to a remote place via a transmission processing unit 6090, such as a telephone line. For example, when the X-ray image is transferred to a doctor's room in a different place, the X-ray image can be displayed on a display 6081 serving as a display unit and can be stored in a recoding medium, such as an optical disk, which enables diagnosis by a doctor in the remote place. For example, in the doctor's room, the X-ray image can be recorded in a film 6110 serving as recording means by a film processor 6100 serving as a recording unit.

The above-described exemplary embodiment of the present invention merely illustrates an example of embodiment for implementing the present invention, and the technical scope of the present invention is not limited thereby. In other words, the present invention can be implemented in various forms without departing from the technical idea or the main features thereof.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation image capturing apparatus, comprising:
a plurality of pixels two-dimensionally arranged in an image capturing area and configured to convert incident radiation into electric signals; and
a plurality of driving lines for driving the plurality of pixels including a first driving line and a second driving line different from the first driving line;
wherein the plurality of pixels includes a plurality of first pixels configured to output the electric signals for acquiring a radiation image and a plurality of second pixels configured to output the electric signals for detecting information about irradiation of the image capturing area with the irradiation,
wherein at least two of the plurality of second pixels which are connected to the first driving line and at least two of the plurality of second pixels which are connected to the second driving line are lined along the first line and the second driving line; and
wherein the first driving line is supplied with a driving signal at a different timing from a timing when the second driving line is supplied with a driving signal.

2. The radiation image capturing apparatus according to claim 1, further comprising:
a readout circuit configured to read out the electric signals of the plurality of pixels,
wherein the readout circuit, at different timings, reads out the electric signals of the plurality of second pixels group by group to each of which a different one of the plurality of driving lines is connected.

3. The radiation image capturing apparatus according to claim 1, further comprising:
a driving signal supply circuit configured to supply a driving signal to each of the plurality of the driving lines connected to the plurality of second pixels at a different timing from each other.

4. The radiation image capturing apparatus according to claim 3, wherein the driving signal supply circuit supplies the driving signal to the plurality of driving lines connected to the plurality of second pixels in sequence.

5. The radiation image capturing apparatus according to claim 3, wherein the driving signal supply circuit further supplies a driving signal to each of the plurality of the driving lines connected to the plurality of first pixels.

6. The radiation image capturing apparatus according to claim 3, wherein the driving signal supply circuit is different from a driving signal supply circuit to supply a driving signal to the plurality of the driving lines connected to the plurality of first pixels.

7. The radiation image capturing apparatus according to claim 1, wherein a number of the plurality of driving lines connected to the plurality of second pixels is two.

8. The radiation image capturing apparatus according to claim 1, wherein the plurality of second pixels are two pixels adjacent in a direction of the driving lines and each of which is connected to a different one of the driving lines.

9. The radiation image capturing apparatus according to claim 1, further comprising:
a readout circuit configured to read out the electric signals of the plurality of pixels via a plurality of signal lines, wherein each of said at least two of the plurality of second pixels connected to the first driving line is connected to a different one of the plurality of signal lines and each of said at least two of the plurality of second pixels connected to the second driving line is connected to a different one of the plurality of signal lines.

10. The radiation image capturing apparatus according to claim 9,
wherein the plurality of signal lines are disposed to intersect with the plurality of driving lines, and
wherein two of the plurality of second pixels adjacent to each other in a direction of the driving lines and two of the plurality of first pixels adjacent to each other in the direction of the driving lines are connected to a single signal line.

11. The radiation image capturing apparatus according to claim 1,
wherein the plurality of second pixels is arranged as line-shaped pixel groups,
wherein a first pixel group of the line-shaped pixel groups is connected to the first driving line and the second driving line, and
wherein a second pixel group of the line-shaped pixel groups is connected to a third driving line and a fourth driving line either of which is different from the first driving line or the second driving line.

12. The radiation image capturing apparatus according to claim 1,
wherein the information about the irradiation with the radiation includes at least one of start of the irradiation of the image capturing area with the radiation, end of the irradiation of the image capturing area with the radiation, intensity of the irradiation of the image capturing area with the radiation or a dose of the irradiation of the image capturing area with the radiation.

13. A radiation image capturing system, comprising:
a radiation image capturing apparatus according to claim 1; and
a processing apparatus configured to process a signal from the radiation image capturing apparatus.

14. The radiation image capturing system according to claim 13,
wherein the processing apparatus stops irradiation with a radiation from a radiation source in accordance with a signal from the radiation image capturing apparatus.

* * * * *